(12) United States Patent
Lee et al.

(10) Patent No.: US 6,509,100 B1
(45) Date of Patent: Jan. 21, 2003

(54) FLUORINATED HYDROGN BOND STABILIZED SURFACE MODIFYING AGENTS, ARTICLES MADE THEREFROM, METHODS FOR MAKING AND USING THE SAME

(75) Inventors: T. Randall Lee, Houston, TX (US); Michael Graupe, San Mateo, CA (US)

(73) Assignee: The University of Houston System, Houston, TX (US)

( * ) Notice: Subject to any disclaimer, the term of this patent is extended or adjusted under 35 U.S.C. 154(b) by 0 days.

(21) Appl. No.: 09/376,878

(22) Filed: Aug. 18, 1999

(51) Int. Cl.$^7$ ................................................. B32B 9/04
(52) U.S. Cl. ..................... 428/447; 428/704; 427/384; 427/387; 530/300; 568/14; 568/16; 568/62; 568/63; 568/65; 562/26; 556/419; 556/420; 556/421; 564/15
(58) Field of Search ................................. 428/447, 704; 427/387, 384; 530/300; 556/419, 420, 421; 564/15, 32, 59, 58; 562/26; 568/14, 16, 62, 63, 65

(56) References Cited

U.S. PATENT DOCUMENTS

| | | | | |
|---|---|---|---|---|
| 3,088,849 A | * | 5/1963 | Friedlander et al. | 117/127 |
| 3,257,407 A | * | 6/1966 | Brace | 260/290 |
| 4,975,363 A | * | 12/1990 | Cavallo et al. | 430/637 |
| 5,202,452 A | * | 4/1993 | Ogawa et al. | 556/435 |
| 5,512,131 A | | 4/1996 | Kumar et al. | 156/655.1 |
| 5,547,711 A | * | 8/1996 | Kirchmeyer et al. | 427/386 |
| 5,620,850 A | | 4/1997 | Bamdad et al. | 530/300 |
| 5,674,671 A | * | 10/1997 | Brandon et al. | 430/527 |
| 5,741,922 A | * | 4/1998 | Yoshino | 556/445 |
| 5,776,748 A | | 7/1998 | Singhvi et al. | 435/180 |
| 5,851,674 A | * | 12/1998 | Pellerite et al. | 428/421 |
| 5,900,160 A | | 5/1999 | Whitesides et al. | 216/41 |
| 5,951,881 A | | 9/1999 | Rogers et al. | 216/41 |
| 5,953,471 A | | 9/1999 | Espindola et al. | 385/37 |
| 5,976,826 A | | 11/1999 | Singhvi et al. | 435/29 |
| 6,048,623 A | | 4/2000 | Everhart et al. | 428/464 |
| 6,132,861 A | * | 10/2000 | Kang et al. | 428/323 |
| 6,153,322 A | * | 11/2000 | Lee et al. | 428/704 |

OTHER PUBLICATIONS

Lenk, et al. "Structural Investigation of Molecular Organization . . ." Langmuir, 1994, 10, 4610–4617.*

Clegg, Robert S. Self–Assembled Monolayers Stabilized by Three–Dimensional Networks of Hydrogen Bonds. Journal of the American Chemical Society. 1998, 120: 2486–2487.

Chechik, Victor. Self–Assembled Monolayers of Branched Thiols and Disulfides on Gold: Surface Coverage, order and Chain Orientation. Langmuir 1998, 14, 3003–3010.

Wegner, G. I. Mitt: Polymerisation von Derivaten des 2.4–Hexadin–1.6–diols im kristallinen Zustand. Topochemische Reakitionen Von Monomeren. pp. 824–832.

Clegg, Robert S. et al. Hydrogen–Bonding, Self–Assembled Monolayers: Ordered Molecular Films for Study of Though– Peptide Electron Transfer. Langmuir, v. 12, pp 5239–5243, 1996.

Suk–Wah Tam–Chang et. al. Self–Assembled Monolayers on Gold Generated from Alkanethiols with the Structure RNHCOCH2SH. Langmuir 1995, 11, 4371–4382.

Lenk, TJ. et al. Structural Investigation of Molecular Organization in Self–Assembled Monolayers of a Semifluorinated Amidethiol. Langmuir 1994, 10, 4610–4617.

Evans, Stephen D., et al. Monolayers Having Large In–Plane Dipole Moments: Characterization of Sulfone–Containing Self–Assembled Monolayers of Alkanethiols on Gold by Fourier Transform Infrared Spectroscopy, X–ray Photoelectron Spectroscopy and Wetting. Langmuir 1991, 7, 2700–2709.

Clegg, Robert S. et al. Control of Monolayer Assembly Structure by Hydrogen Bonding Rather Than by Adsorbate–Substrate Templating. Journal of the American Chemical Society 1991, 121, 5319–5327.

Sabapathy, Rajaram C. et al. Electrochemical and Spectroscopic Caracterization of Self–Assembled Monolayers of Ferrocenylalkyl Compounds with Amide Linkages. Langmuir 1998, 14, 124–136.

Clegg, Robert S., et al. Self–Assembled Monolayers Stabilized by Three–Dimensional Networks of Hydrogen Bonds. Journal of the American Chemical Society 1998, 120, 2486–2487.

* cited by examiner

*Primary Examiner*—Margaret G. Moore
(74) *Attorney, Agent, or Firm*—Robert W. Strozier

(57) ABSTRACT

The present invention discloses hydrogen bond stabilized surface modifying agents having a fluorinated or semifluorinated carbon-containing tail group, an internal moiety capable of intermolecular hydrogen bonding or related acid-base interactions and a head group capable of reacting or interacting with surfaces such as metal, non-metallic, ceramic, other inorganic oxide or organic surfaces. The present invention also discloses cost effective method for making the agents, methods for treating surfaces therewith, the treated surfaces and devices made therefrom.

27 Claims, 1 Drawing Sheet

FLUORINATED HYDROGN BOND STABILIZED SURFACE MODIFYING AGENTS, ARTICLES MADE THEREFROM, METHODS FOR MAKING AND USING THE SAME

BACKGROUND Of THE INVENTION

1. Field of the Invention

This invention relates to hydrogen bond stabilized surface modifying agents (HB-SMAs), surfaces treated with the agents, methods for treating surfaces to impart non-wettable, non-stick, friction-reducing, corrosion resistant, or other properties to the surfaces and methods for making the agents.

More particularly, the present invention relates to hydrogen bond stabilized surface modifying agents where the stability results from intermolecular hydrogen bonding between adjacent surface modifying agents, surfaces treated with the agents, methods for treating surfaces and methods for making the hydrogen bond stabilized surface modifying agents of this invention.

2. Description of the Related Art

The synthesis of long chain α,ω-functionalized semifluorinated hydrocarbons, where α and ω are integers that describe the positions of specific functional groups along the fluorohydrocarbon backbone, remains a challenging enterprise for interfacial scientists. The generation of organized thin films from these molecules offers the opportunity to study and manipulate fundamental properties of fluorinated interfaces, such as wetting, adhesion, and tribology. The ability to control the identities of the α,ω-functionalities using organic synthesis permits atomic-level control over the structure and composition of interfaces formed from these molecules using self-assembly techniques. Organic synthesis thus provides a convenient tool for fine-tuning the interfacial properties.

Several methods have been utilized for the preparation of compounds having perfluorinated terminal segments.[1-6] Many approaches have been designed to yield target molecules containing a terminal $CF_3$ group.[7-16] A limited number ofmethods have, however, provided the opportunity to introduce fluorinated segments of differing lengths.

Brace, for example, investigated the radical addition of several iodoperfluorinates to allylacetate.[1,2] This approach was based on initial studies by Park and Lacher[17] and Moore,[18] which utilized ultraviolet light as the radical source. By employing an azo initiator, however, Brace was able to complete the reaction within a few hours compared to five days when using UV light. Brace and previous investigators[19,20] proposed that the reaction proceeded through the formation of a perfluoroalkyl radical that attacked the terminal carbon of the olefinic group. Reduction of the resultant fluorinated iodoacetate with zinc or $LiAlH_4$ provided a variety of perfluoroalkylated compounds in excellent yields.[2]

Cloux and Kovats modified the approach developed by Brace to include the addition of2,2,2-trifluoroethyl iodide to terminal alkenes.[21] 2,2,2-Trifluoroethyl iodide is a liquid and made handling the reaction easier than the reaction using gaseous trifluoromethyl iodide. The authors noted that microanalyses failed to give correct and reproducible results.

Several groups have shown that thiol-terminated reagents can be used to modify the interfacial properties of metallic surfaces due to the strong interaction between the thiol moiety and the metal atoms of the surface.[22-24] Other related strategies for modifying the properties of both metallic and non-metallic surfaces are also known.[22-24]

Although the radical coupling of T-alkenyl acetates with "-halo-fluorinated hydrocarbons has been reported, and surface modification strategies involving intermolecular H-bonded hydrocarbon adsorbates have been reported,[25] there still exists a need in the industry for a cost effective, high yield and versatile method for making fluorinated surface modifying agents (e.g., fluorinated alkanethiols or disulfides) and their precursors that can be used to control surface characteristics, imparting, for example, corrosion-resistant, non-wettable, non-stick, or low frictional properties to the surfaces.

SUMMARY OF THE INVENTION

The present invention provides hydrogen bond stabilized surface modifying agents (HB-SMAs) including at least one fluorine and carbon-containing tail group, at least one surface reactive head group and at least one hydrogen bonding group interposed between the head and tail groups. The surface modifying agents are used to coat metallic, ceramic or other surfaces to influence, change, augment or enhance the surface characteristics of the material.

The present invention provides HB-SMAs represented by Formula (I):

$$(R_f)_\alpha\text{-}\chi\text{-}(Q)_\beta \qquad (I)$$

where:

$R_f$ is a carbon-containing head group including at least one fluorine atom;

$\chi$ is a carbon-containing group including at least one moiety or functional group capable of intermolecular hydrogen bonding or related acid-base interaction;

Q is a tail group including at least a N atom, an O atom, a Si atom, a P atom or a S atom;

α and β are integers the sum of which does not exceed the maximum number of substituents χ can accomodate. χ can further include a multivalent moiety R", where R" is a tetravalent atom, carbon-carbon double bond or a ring system.

The present invention provides a preferred class ofHB-SMAs represented by Formula (III):

$$R_f\chi\text{-}Q \qquad (III)$$

where $R_f$, χ and Q are as previously defined.

The present invention also provides a preferred class of HB-SMAs represented by Formula (III) where $R_f$ is as previously defined and where:

χ is $R^{HB}$, $R^1\text{-}R^{HB}$, $R^{HB}\text{-}R^1$, $R^1\text{-}R^{HB}\text{-}R^{XL}$, $R^{HB}\text{-}R^1\text{-}R^{XL}$, $R^{HB}\text{-}R^{XL}\text{-}R^1$, $R^1\text{-}R^{XL}\text{-}R^{HB}$, $R^{XL}\text{-}R^1\text{-}R^{HB}$, $R^{XL}\text{-}R^{HB}\text{-}R^1$, $R^1\text{-}R^{HB}\text{-}R^2$, $R^1\text{-}R^{HB}\text{-}R^2\text{-}R^{XL}$, $R^{HB}\text{-}R^1\text{-}R^{XL}\text{-}R^2$, $R^1\text{-}R^{XL}\text{-}R^2\text{-}R^{HB}$, $R^{XL}\text{-}R^1\text{-}R^{HB}\text{-}R^2$, or combinations or mixtures thereof, where:

$R^1$ and $R^2$ are the same or different and are carbon-containing groups;

$R^{HB}$ is a group including a peptide linkage (—C(O)N(H)—), urethane linkage (—O—C(O)—N(H)—), urea linkage (—N(H)—C(O)—N(H)—) or mixtures or combination thereof; and $R^{XL}$ is a crosslinkable group including an acetylenic group, a diacetylenic group, polyacetylenic group, an alpha amino acid group, an alpha hydroxy acid group or a dialkoxysilenyl group; and Q is $NR^3$, $OR^3$, $SiR^3$, $SiOR^3$, $PR^3$, $SR^3$ or $CE^1E^2$, where:
$R^3$ is a hydrogen atom or a carbon containing group, and
$E^1$ is $NR^4$, O, $PR^4$ or S,
$E^2$ is $R^4$, $NR^4_2$, $OR^4$, $PR^4_2$, or $SR^4$; and where:
each $R^4$ is the same or different and is a hydrogen atom or a carbon-containing group.

The present invention also provides a dimeric HB-SMAs of Formula (IV):

$$R_f\text{-}\chi\text{-}QQ'\text{-}\chi'R_f' \qquad (IV)$$

where $R_f$ and $R_f'$, R and R', $\chi$ and $\chi'$ and Q and Q' are the same or different groups as defined previously.

This invention also provides methods for making HB-SMAs of Formulas (I–IV).

This invention also provides a method for treating surfaces of substrates including contacting the substrate or substrate surface(s) with at least one agent of Formulas (I–IV) in an amount sufficient to form a partial or complete monolayer of the agent thereon.

This invention also provides a method for treating a surface including contacting a surface with at least one agent of Formulas (I–IV) to form a partial or complete monolayer of the agent thereon.

The present invention also provides a substrate including a surface having a partial or complete monolayer formed of at least one agent of Formulas (I–IV).

The present invention also provides devices or apparatus incorporating a substrate including a surface having a partial or complete monolayer formed of at least one agent of Formulas (I–IV).

BRIEF DESCRIPTION OF DRAWINGS

The invention can be better understood with reference to the following detailed description together with the appended drawings in which like elements are numbered the same.

DESCRIPTION OF THE PREFERRED EMBODIMENTS

Figure 1:
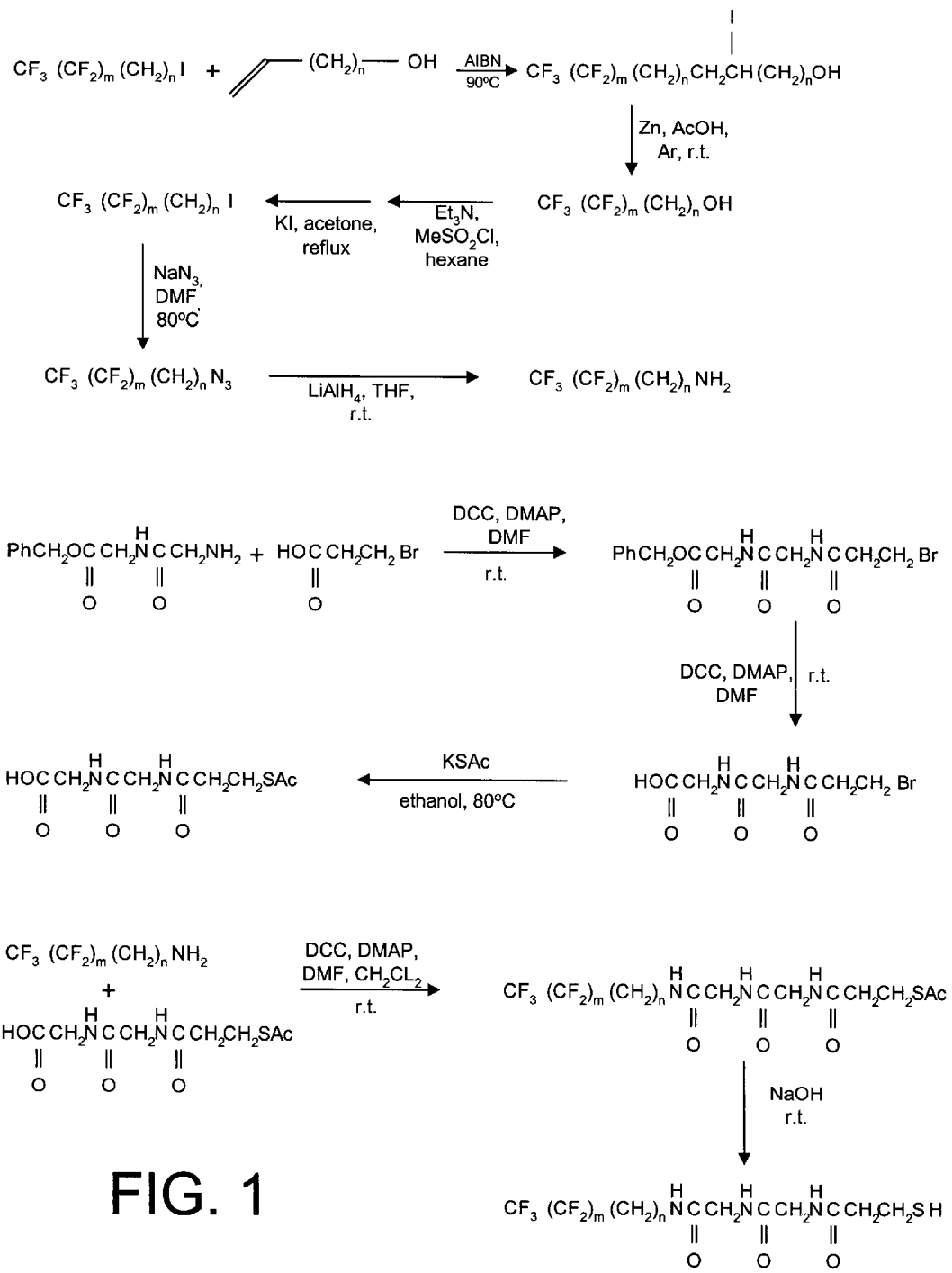
FIG. 1 depicts a preferred synthetic scheme for making one preferred class of surface modifying agents of the present invention.

The inventors have found that a surface modifying agents having a semifluorinated carbon-containing tail group and a surface reactive head group that can form self-assembled monolayers on surfaces that are stabilized and rendered capable of withstanding temperatures above about 100° C. and preferably temperatures above about 150° C. and especially greater than or equal to 200° C. through the inclusion of a moiety or molecular region capable of intermolecular hydrogen bonding or related intermolecular interactions. The head group or moiety generally contains at least one nitrogen atom, oxygen atom, phosphorus atom, silicon atom, or sulfur atom. The agents are designed to react with surfaces forming partial or complete mono-molecular layers on the surface, thereby modifying the surface characteristics. Because the tail group of the agent, the part extending away from the surface, consists of a fluorinated or semifluorinated moiety, the partial or complete mono-molecular layer (monolayer) generally imparts non-wettable, non-stick, or low frictionals characteristics to the surface. The hydrogen bonding region imparts enhanced thermal and mechanical stability to monolayers forms on a surface because the individual molecules of the monolayer form intermolecular hydrogen bonds.

Although the surface modifying agents of the present invention generally react chemically with the surfaces they are intended to treat, the exact nature of the reaction of the head group(s) of the agent with the surface will depend on the nature of the surface being treated, the treating agent and its head group. In certain circumstances, the exact nature of the bonding may not be well characterized or understood. Therefore, the inventors use the terms "reactive" or "reacted with" to include any type of interaction between a head group of an agent and the surface that gives rise to the formation of interfacial monolayers.

Generally, however, the nature of the reaction and interaction between the head group and surface moieties will be some type of physical and/or chemical absorption, adsorption and/or chemical bonding process or mechanism, preferably the reaction or interaction will be a chemical bond including, without limitation, a covalent bond, ionic bond, coordinate bond, hydrogen bond, polar bond, apolar bond or other bonding interaction or mixtures or combinations thereof.

Hydrogen Bond Stabilized SMAs

The present invention provides hydrogen bond stabilized surface modifying agents that have at least one semifluorinated carbon-containing tail group, at least one hydrogen bonding region and at least one surface reactive head group. The surface modifying agents are used to coat metallic, ceramic, or other surfaces to influence, change, augment, or enhance the surface characteristics of the material.

The present invention relates to HB-SMAs represented by Formula (I):

$$(R_f)_\alpha\text{-}\chi\text{-}(Q)_\beta \qquad (I)$$

where:
$R_f$ is a carbon-containing head group including at least one fluorine atom;
$\chi$ is a carbon-containing group including at least one moiety or functional group, $R^{HB}$, capable of intermolecular hydrogen bonding or related acid-base interaction and optionally at least one $R^{XL}$ group, where:
$R^{HB}$ is a group including a peptide linkage (—C(O)N(H)—), urethane linkage (—O—C(O)—N(H)—), urea linkage (—N(H)—C(O)—N(H)—) or mixtures or combinations thereof; and
$R^{XL}$ is a crosslinkable group including an acetylenic group, a diacetylenic group, polyacetylenic group, an alpha amino acid group, an alpha hydroxy acid, a dialkoxysilenyl group or mixtures or combination thereof; and
Q is a tail group including at least a N atom, an O atom, a SI atom, a P atom or a S atom and is generally an $NR^3$, $OR^3$, $SiR^3$, $SiOR^3$, $PR^3$, $SR^3$ or $CE^1E^2$ group where:
$R^3$ is a hydrogen atom or a carbon containing group, and
$E^1$ is $NR^4$, O, $PR^4$ or S,
$E^2$ is $R^4$, $NR_2^4$, $OR^{42}$, $PR^4_2$, or $SR^4$; and where:
each $R^4$ is the same or different and is a hydrogen atom or a carbon-containing group; and
$\alpha$ and $\beta$ are integers the sum of which does not exceed the maximum number of substituents $\chi$ can accomodate.

The present invention relates to a preferred class of HB-SMAs represented by Formula (II):

$$(R_f)_2\text{-}\chi\text{-}(Q)_2 \qquad (II)$$

where $R_f$, $\chi$ and Q are as previously defined.

The present invention relates to another preferred class of HB-SMAs represented by Formula (III):

$$R_f\text{-}\chi\text{-}Q \tag{III}$$

where $R_f$, $\chi$ and Q are as previously defined.

The present invention relates to another preferred class of HB-SMAs represented by Formula (III), where $R_f$, and Q are as previously defined and where:

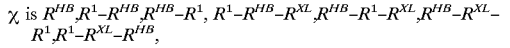
$\chi$ is $R^{HB}, R^1\text{-}R^{HB}, R^{HB}\text{-}R^1, R^1\text{-}R^{HB}\text{-}R^{XL}, R^{HB}\text{-}R^1\text{-}R^{XL}, R^{HB}\text{-}R^{XL}\text{-}R^1, R^1\text{-}R^{XL}\text{-}R^{HB}$,

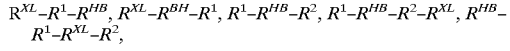
$R^{XL}\text{-}R^1\text{-}R^{HB}, R^{XL}\text{-}R^{BH}\text{-}R^1, R^1\text{-}R^{HB}\text{-}R^2, R^1\text{-}R^{HB}\text{-}R^2\text{-}R^{XL}, R^{HB}\text{-}R^1\text{-}R^{XL}\text{-}R^2$,

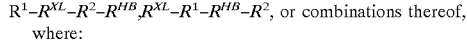
$R^1\text{-}R^{XL}\text{-}R^2\text{-}R^{HB}, R^{XL}\text{-}R^1\text{-}R^{HB}\text{-}R^2$, or combinations thereof, where:

$R^1$ and $R^2$ are the same or different and are carbon-containing groups and $R^{HB}$ and $R^{XL}$ are as previously defined.

Besides monomeric agents of Formula (I), the present invention also relates to dimeric products of Formula (IV):

$$R_f\text{-}\chi\text{-}QQ'\text{-}\chi'\text{-}R_f' \tag{IV}$$

where $R_f$ and $R_f'$ and $\chi$ and $\chi'$ and Q and Q' are the same or different groups as defined previously.

Preferred Monomeric SMAs

The present invention also relates to monomeric products of Formula (V):

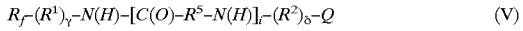
$$R_f\text{-}(R^1)_\gamma\text{-}N(H)\text{-}[C(O)\text{-}R^5\text{-}N(H)]_i\text{-}(R^2)_\delta\text{-}Q \tag{V}$$

where $R^{HB}$ comprises at least two amide linkages, $R_f$, Q, $R^1$ and $R^2$ are as previously defined and $R^5$ is a carbon-containing group, i is an integer having a value between 1 and about 10, $\gamma$ is an integer having a value of 0 or 1 and $\delta$ is an integer having a value of 0 or 1.

The present invention also relates to monomeric products of Formula (VI):

$$R_f\text{-}(R^1)_\gamma[C(O)\text{-}N(H)\text{-}R^5]_i\text{-}(R^2)_\delta Q \tag{VI}$$

where $R_f$, Q, $R^1$, $R^2$, $R^5$, i, $\gamma$ and $\delta$ are as previously defined.

The present invention also relates to monomeric products of Formula (VII):

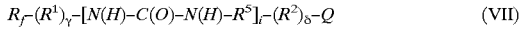
$$R_f\text{-}(R^1)_\gamma\text{-}[N(H)\text{-}C(O)\text{-}N(H)\text{-}R^5]_i\text{-}(R^2)_\delta\text{-}Q \tag{VII}$$

where $R_f$, Q, $R^1$, $R^2$, $R^5$, i, $\gamma$ and $\delta$ are as previously defined.

The present invention also relates to monomeric products of Formula (VIII):

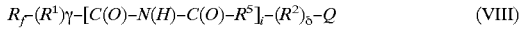
$$R_f\text{-}(R^1)\gamma\text{-}[C(O)\text{-}N(H)\text{-}C(O)\text{-}R^5]_i\text{-}(R^2)_\delta\text{-}Q \tag{VIII}$$

where $R_f$, Q, $R^1$, $R^2$, $R^5$, i, $\delta$ and $\delta$ are as previously defined.

The present invention also relates to monomeric products of Formula (IX):

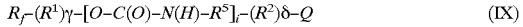
$$R_f\text{-}(R^1)\gamma\text{-}[O\text{-}C(O)\text{-}N(H)\text{-}R^5]_i\text{-}(R^2)\delta\text{-}Q \tag{IX}$$

where $R_f$, Q, $R^1$, $R^2$, $R^5$, i, $\gamma$ and $\delta$ are as previously defined.

The present invention also relates to monomeric products of Formula (X):

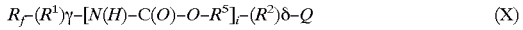
$$R_f\text{-}(R^1)\gamma\text{-}[N(H)\text{-}C(O)\text{-}O\text{-}R^5]_i\text{-}(R^2)\delta\text{-}Q \tag{X}$$

where $R_f$, Q, $R^1$, $R^2$, $R^5$, i, $\gamma$ and $\delta$ are as previously defined.

When forming a hydrogen bonding complete or partial monolayer of an agent of formulas (V–X), it is preferred to use a mixture of NH initiated sequences and CO initiated sequences having a similar or compatible structure so that the NH and CO groups are staggered enhancing hydrogen bonding interactions and increasing layer stability.

Multiply Stabilized SMAs

This invention also addresses agents that rely on several bonding mechanisms to stabilize the monolayer on a substrate surface. The preferred classes of these multi-functional intermolecular bond stabilized agents include at least one hydrogen bonding region and at least one crosslinkable region.

Three preferred classes of these multi-functional surface modifying agents including diacetylenic crosslinkable groups Formulas (II), (III) and (IV):

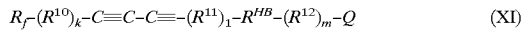
$$R_f\text{-}(R^{10})_k\text{-}C{\equiv}C\text{-}C{\equiv}\text{-}(R^{11})_1\text{-}R^{HB}\text{-}(R^{12})_m\text{-}Q \tag{XI}$$

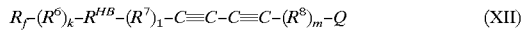
$$R_f\text{-}(R^6)_k\text{-}R^{HB}\text{-}(R^7)_1\text{-}C{\equiv}C\text{-}C{\equiv}C\text{-}(R^8)_m\text{-}Q \tag{XII}$$

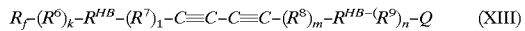
$$R_f\text{-}(R^6)_k\text{-}R^{HB}\text{-}(R^7)_1\text{-}C{\equiv}C\text{-}C{\equiv}C\text{-}(R^8)_m\text{-}R^{HB\text{-}}(R^9)_n\text{-}Q \tag{XIII}$$

where $R_f$, $R^{HB}$, Q are as previously defined and $R^6$, $R^7$, $R^8$ and $R^9$ are carbon containing groups and k, 1, m and n are integers having a value of either 0 or 1.

Methods for Making HB-SMAs The method for making HB-SMAs of Formula (I) of this invention generally involves a synthetic scheme as shown below:

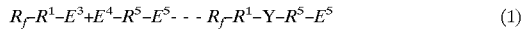
$$R_f\text{-}R^1\text{-}E^3+E^4\text{-}R^5\text{-}E^5\text{-}\text{-}\text{-}R_f\text{-}R^1\text{-}Y\text{-}R^5\text{-}E^5 \tag{1}$$

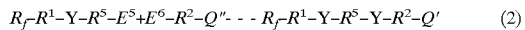
$$R_f\text{-}R^1\text{-}Y\text{-}R^5\text{-}E^5+E^6\text{-}R^2\text{-}Q''\text{-}\text{-}\text{-}R_f\text{-}R^1\text{-}Y\text{-}R^5\text{-}Y\text{-}R^2\text{-}Q' \tag{2}$$

where $R^1$, $R^2$ and $R^5$ and $E^3$, $E^4$, $E^5$ and $E^6$ are a COOH, COX, COOR$^{10}$ or NH$_2$ paired so that $E^3$ and $E^4$ and $E^5$ and $E^6$ condense to form a linkage Y, where Y is the same or different linkage and are a peptide linkage, (—C(O)N(H)—), urethane linkage, (—O—C(O)—N(H)—) or urea linkage, (—N(H)—C(O)—N(H)—). Additionally, Q" is a either Q or a protected Q so that Q does not enter into the condensation reaction shown in step (2). Such blocking groups are will known to those skilled in the art such as an acetate group or similar blocking or protecting groups.

Alternatively, the HB-SMAs of Formula (I) of this invention can be made by the following synthetic scheme:

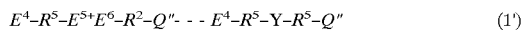
$$E^4\text{-}R^5\text{-}E^{5*}E^6\text{-}R^2\text{-}Q''\text{-}\text{-}\text{-}E^4\text{-}R^5\text{-}Y\text{-}R^5\text{-}Q'' \tag{1'}$$

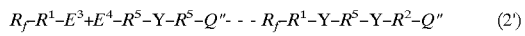
$$R_f\text{-}R^1\text{-}E^3+E^4\text{-}R^5\text{-}Y\text{-}R^5\text{-}Q''\text{-}\text{-}\text{-}R_f\text{-}R^1\text{-}Y\text{-}R^5\text{-}Y\text{-}R^2\text{-}Q'' \tag{2'}$$

where $R^1$, $R^2$, $R^5$, $E^3$, $E^4$, $E^5$, Y and Q" are as previously defined.

One preferred synthetic scheme for forming the $R_f\text{-}R\text{-}E^3$ reactant involves radically coupling an α-hydroxy-ω-alkene with an ω-iodo-fluorinated hydrocarbon to form an ω-hydroxyfluorinated hydrocarbon. The ω-hydroxyfluorinated hydrocarbon can be used directly or converted into an ω-aminofluorinated hydrocarbon. Alternatively, the ω-iodo-fluorinated can be reacted with an alkyl lithium reagent and then with carbon dioxide to yield an ω-carboxylic acid of the fluorinated hydrocarbon.

Yet another synthetic scheme for making the HB-SMAs of the present invention is described in FIG. 1. Of course, some of the synthetic procedures set forth in FIG. 1 can be modified as is well known in the art.

Methods for Making HB-SMAs and Crosslinkable HB-SMAs

The general synthetic scheme involves the reaction of bis(trimethylsilyl)diacetylene with a MeLi-LiBr complex in THF. After addition of the MeLi-LiBr complex, RfX (X=I, Br or Cl) in the presence of HMPA is added to the reaction mixture followed by KF in DMF (dimethylformamide) resulting in the formation of intermediate $R_f$-C≡C-C≡C-H. The $R_f$-C≡C-C≡C-H intermediate is then reacted with n-BuLi in THF followed by the addition of an α,ω-dibromoalkane to yield intermediate $R_f$-C≡C-C≡C-RBr. The $R_f$-C≡C-C≡C-RBr intermediate is then reacted with $NH_3$ in ethanol under sonication and worked up under acid conditions to yield crosslinkable ω-amino fluorinated hydrocarbon reagent for use in the synthetic schemes for forming the HB-SMAs set forth in the previous section. Alternatively, the $R_f$-C≡C-C≡C-RBr intermediate can be reacted with appropriate oxygen, silicon or phosphorus reagents to yield other crosslinkable, hydrogen bond stabilized surface modifying agents of Formula (I).

Methods for Treating Surfaces with HB-SMAs

This invention also provides a method for treating surfaces of substrates including contacting the substrate surface (s) with at least one agent of Formula (I) in an amount sufficient to form a partial or complete monolayer of the agent thereon. This invention also provides a method for treating surfaces including contacting a surface with at least one agent of Formula (I) to form a partial or complete monolayer of the agent thereon.

The present invention also provides a substrate including a surface having a partial or complete monolayer formed of at least one agent of Formula (I). Devices or apparatus include, without limitations, any device or apparatus that has a surface or a component with a surface that would perform better for its intended purpose if the surface was coated with a surface modifying agent of the present invention.

Surfaces including, without limitation, metallic surfaces, non-metallic surfaces such as organic surfaces, inorganic surfaces, ceramic surfaces, ceramic fiber surfaces, organic fiber surfaces or inorganic fiber surfaces, or other similar modifiable surfaces can be modified with at least one agent of the global Formula (I) by contacting the surface with at least one of these agents.

When the surface is a metallic surface, then Q is a group that reacts or interacts with the metal atoms at or near the surface to form a partial or complete monolayer of the agent on the metallic surface. In the case of metallic surfaces, Q preferably contains N, O, P or S.

When the surface is a non-metallic surface, the Q reacts or interacts with active sites on the surface to form a partial or complete monolayer of the agent on the non-metallic surface. In the case of non-metallic surfaces such as ceramic surface or other inorganic surfaces, Q preferably contains N, O, P, S, Zr or Si. In the case of organic surfaces or organic fiber surfaces, Q is selected to react with exposed reactive sites on the organic surface or fiber surface such as a COOH group, OH group, NH group or the like.

By "surface", the inventor means atoms or sites directly on the surface and atoms or sites about 1 to about 10 atomic or molecular layers below the surface. Thus, the surface modifying agents can react or interact with atoms or sites directly on the surface or near the surface (slightly below the interface). An ordinary artisan should recognize that surfaces generally have holes, breaks, cracks, crevices or the like associated therewith and the surface modifying agents would be expected to react or interact anywhere on the surface or near the surface or any accessible site on surface. The inventors, therefore, are not limiting the reactions or interactions of the surface modifying agents of Formula (I) to atoms or sites forming the interface between the surfaces of an object and their surroundings; provided, of course, that the $R_f$ group of the agents extends out from the "surface" of the modified object or material.

These treated surfaces with a partial or complete monolayer of surface modifying agents of Formula (I) thereon can be used for any non-stick application, non-wetting application, corrosion inhibiting application, and/or friction reducing application. Because the surface modifying agents of Formula (I) have an $R_f$ moiety associated with the end of the agent not bound to the surface and because such $R_f$ moieties are known to reduce attractive chemical and physical interactions, the partial or complete monolayers impart a non-stick, non-wettable, low friction coating which is essential in improving flow characteristics of materials over the treated surfaces, in reducing friction between objects that contact the treated surface, in improving corrosion resistance of treated surfaces, or in reducing potential build up of the material on the treated surfaces.

These treated surfaces will generally result in contact angles with deionized water of between about 80° and about 180°, with angles between about 100° and about 150° being particularly preferred and angles between about 110° and about 130° being especially preferred. Of course, certain of these surfaces can have contact angles approaching 180° for rough, amorphous surfaces (i.e., where the water droplet forms spherical bead on the surface).

Alternately, for metals that form stable oxides or for any other type of surface, the surface to be treated can be coated with a metal that does not form a stable oxide such as gold. Gold-coated surfaces can then be contacted with at least one surface modifying agent of Formula (I) to impart a non-stick, low friction partial or complete monolayer of the agent(s) on the gold-coated surface. For most non-metallic surfaces, the appropriate agents, those that will react and/or interact strongly with active sites on the surface, can simply be brought in contact with the surface, either neat or in an appropriate solvent, by any method well-known in the art, including dipping, spraying, soaking, vapor depositing, touching, wiping, washing, or the like.

The treating of a surface with at least one agent of Formula (I) can generally be performed by contacting the surface with a millimolar solution of the agent in an appropriate solvent. The step of contacting can include dipping, spraying, soaking, vapor depositing, touching, wiping, washing, or any other similar method for bringing the surface into contact with the modifying agent(s). Additionally, the amount of agents used are sufficient of achieve the desired surface coverage. Preferably, an excess of agent is used to ensure complete monolayer formation.

Besides being surface modifying agents for organic surfaces, organic fiber surfaces, ceramic surfaces or ceramic fiber surfaces, the agents of Formula (I) where Q contains N or O may have application in other synthetic processes where fluorinated amines or alcohols could be used to augment the physical and chemical properties of desired products. The amine and oxidized S-containing or P-containing agents can be used to produce L-B films, surfactants, or the like. While the alcohols and amines can be used to terminate condensation polymers or the like.

Although the compounds of Formula (I) where Q contains only O or N typically do not form stable surface modifications on metallic surfaces as compared to compounds of Formulas (I) where Q contains S or P, the former compounds can be easily converted into metallic surface modifying agents where Q is S or P using standard reactions well-known in the art.

Devices Including Surfaces Treated with HB-SMAs

Device surfaces can be treated directly with one or more agents of Formula (I). In the case of metal surfaces that form stable oxides, the surface is preferably treated when the surface is substantially free of surface oxides, which in some cases reduces the efficiency of surface modification. Maintaining an oxide-free surface can be difficult requiring that the surface modifying agents be applied in an inert atmosphere such as by dipping the oxide-free surface in the agents neat or in an appropriate solvent. The surface modifying agents can also be sprayed onto the surface, vapor deposited onto the surface or applied in any other way commonly known in the art. The present invention is also directed to devices and components having at least one surface comprising a partial or complete monolayer of an HB-SMA of Formula (I) such as aerosol nozzles, spray nozzles, squirt nozzles, ink-jet printer nozzles, computer hard disk surfaces, semi-conductor surfaces, microelectromechanical (MEM) surfaces, bio-material surfaces or the like.

Suitable Groups, Reagents and Solvents

Suitable $R_f$ groups include, without limitation, any group containing at least one (one or more) C-F bond. These groups include, without limitation, fluorinated alkyl groups, fluorinated aryl groups, fluorinated ara alkyl groups, fluorinated alka aryl groups, fluorinated alkyl-alkylene oxide groups, fluorinated alkyl-alkylene amine groups, or other fluorinated groups including an alkyl moiety and a hetero atom containing moiety. Preferred, fluorinated alkyl, ara alkyl and alka aryl groups are described by the general formula $C_pF_qH_r$ where p, q and r are integers and q+r is equal to one less than the maximum number of hydrogen atoms that would be needed to complete the bonding valences of the carbons atoms in the group and q>1, i.e., the group has at least one F atom associated therewith. The alkyl moiety can be linear or branched. If the fluorinated group is a fluorinated linear alkyl group, then q+r=2p-1 and q>1.

More preferably in the agents of Formula (I), $R_f$ is a fluorocarbon group having the following general formula $CF_3(CF_2)_s(CH_2)_t$ where s is an integer having a value between 0 and about 30 and t is an integer having a value between 0 and about 50. Preferably, s is between 0 and about 20, and particularly, between about 0 and about 18, especially between about 5 and about 15. Preferably, t is between and 0 and about 40, and particularly, t is between about 0 and about 35. When $R_f$ includes atoms other than carbon, hydrogen and fluorine, the other atoms generally should not be substantially susceptible to radical addition or abstraction reactions and should be stable to chemical reduction under the conditions described in the preparation of the surface modifying agents of Formula (I) as described herein.

It should be recognized that although preferred ranges for the fluorinated carbon-containing groups are given, the particular choice of p, q, r, s and t for the group will depend on the purpose to which the surface to be treated is to be used. In some applications, a short perfluorinated-head group could be used, while in other applications longer perfluorinated- head groups may be preferred.

Suitable $R^{1-2}$ and $R^{5-9}$ groups include, without limitation, linear or branched moieties of the general formula $(CH_2)_{pp}$, where pp is an integer having a value between about 0 and about 50, a branched alkenyl group, an alkenyl aryl group, an ara alkenyl group or the like. Preferred $R^{1-2}$ and $R^{5-9}$ groups include $(CH_2)_{pp}$ groups where pp is an integer having a value between about 0 and about 40. The $R^{1-2}$ and $R^{5-9}$ groups can also include atoms other than carbon and hydrogen. Preferred groups including oxygen are groups including one or more methylene oxide or ethylene oxide moieties in the carbon chain. Alkylated amine groups in the carbon chain are also useful $R^{1-2}$ and $R^{5-9}$ groups. Such $R^{1-2}$ and $R^{5-9}$ groups including non-carbon atoms should also not be substantially susceptible to radical addition or abstraction reactions. $R^{1-2}$ and $R^{5-9}$ are preferably a linear group to enhance the packing of the surface modifying agent on the treated surface. Preferably, $R^1$ and $R^2$ are linear carbon-containing groups having been 1 and 20 carbon atoms.

Suitable $R^{3-4}$ and $R^{10}$ groups include, without limitation, alkyl groups, aryl groups, ara alkyl groups, alka aryl groups, heteroalkyl groups, heteroaryl groups or the like. In fact, $R^{3-4}$ and $R^{10}$ can be any group that does not interfere with the reactions described herein.

Suitable reducing agents for use in the present invention include, without limitation, borohydrides such as sodium borohydride, lithium triethyl borohydride, or the like, aluminohydrides such as lithium aluminum hydride or the like or any metal-based reducing agent. Although boro and alumino hydrides are preferred, any other reducing agent that does not interfere with the indicated transformations can also be used.

Suitable deblocking agents include, without limitation, strong acids such as HCl, $H_2SO_4$ or the like and bases such as amines, alkoxides or carbonates. Of course, other acids or bases can be used.

Suitable solvents for treating surfaces with the agents of Formula (I) include, without limitations, hydrocarbon solvents such as hexane, octane, isooctane or the like, chlorinated solvents such as methylene chloride, trichloroethane, or the like, alcohols such as methanol, ethanol, isopropanol, or the like or ethers such as diethylether, THF or the like or water-based solvent systems such as water, water-surfactant mixtures or the like. Of course, any solvent or mixture of solvents can be used provided that the solvent or solvent mixture allows the surface modifying agent to react with the surface to be treated. Under this broad definition, slurries, emulsions, dispersions, solutions, or mixtures thereof can be used as the carrier in the surface treating step.

Suitable radical initiators useful in the radical coupling reactions used in the invention include, without limitation, azo initiators such as AIBN or the like, peroxides such as benzoylperoxide or the like, hydroperoxides such benzoyl-hydroperoxide or the like, ionizing radiation, or other radical initiators, or mixtures or combinations thereof.

EXAMPLES

The following examples are included to illustrate the synthetic methodology disclosed in the present invention and are not meant to be construed as a limitation to the synthetic method.

General Information

Nuclear magnetic resonance spectra ($^1$H and $^{13}$C NMR) were recorded on a GE-300 (300 MHZ) spectrometer using chloroform-d as the solvent. Chemical shifts are reported in units of part per million downfield from tetramethylsilane (0.0) using the residual solvent signal as an internal standard. All coupling constants are reported in units of Hertz (Hz). Reactions were monitored by thin layer chromatography (TLC) using Whatman F 254 precoated silica gel plates (0.25 mm thickness). EM silica gel (63–200 μm, 35–70 μm) and reagent grade solvents were used for column chromatography and medium pressure liquid chromatography (MPLC). Anhydrous solvents were dried by passing through activated alumina and degassed by the freeze-pump-thaw method immediately prior to use.

Example 1

This example illustrates the synthesis of $CF_3(CF_2)_3(CH_2)_{11}NH_2$ which is a general precursor for making surface modifying agents of the present invention with a beginning amino functional group, i.e., $R_f$—R—NH—$R^{HB}$—R'—SH. The synthesis involved a four step synthesis in which an alkene was radically coupled to an α—$R_f$—ω-iodo-alkane to form an α-$R_f$-ω-hydroxy-alkane. The ω-alcohol was then mesylated and converted to an α—$R_f$—ω-iodoalkane. The iodo intermediate was then reacted with sodium azide to form an ω-azide intermediate which was reduced to form the α—$R_f$—ω-aminoalkane starting compound for making surface modifying agents of the present invention.

Step 1 Illustrates the Synthesis of $CF_3(CF_2)_3(CH_2)_{11}OH$

ω-undecylenyl alcohol (65.0 mmol) and 1-iodononafluorobutane (71.5 inmol) were placed in 50 mL Schlenk flask, and the radical initiator AIBN (0.2 mol. %) was added under flow of argon. The flask was closed, evacuated until the bubbling stopped, and refilled with argon; this process was repeated at least two additional times. The flask was sealed under vacuum, and the stirred reaction mixture was heated to 90° C. After 3 hours, the flask was cooled to room temperature, and another portion of AIBN was added under flow of argon. The stirred solution was again heated to 90° C. and this process was repeated at least two additional times. The flask was cooled to room temperature and the crude iodoalcohol was used in the next step without further purification. $^1$H—NMR (CDC13): 4.31 (m, 1H), 3.63 (t, 2H), 3.0–2.8 (m, 2H), 1.65–1.50 (m, 4H), 1.41–1.22 (m, 12H).

The crude iodoalcohol from step 1 was dissolved in 50 mL of glacial acetic acid (HOAc). Zinc dust (130.0 mmol) was added atroom temperature under argon. The mixture was stirred for overnight and then a little water and ether were added to mixture and it was filtered though Celite. Water and ether was added to the filtrate, organic part was washed with water (2×100 mL), saturated NaHCO3 (1×100 mL), and brine (1×100 mL), and then dried over MgSO4. Then the solvent was evaporated and re-crystallization from hexane fluorinated alcohol was produced as white powder. $^1$H—NMR (CDC13): 3.63 (t, 2H), 2.1–1.9 (m, 2H), 1.60 (m, 4H), 1.29 (m, 14H).

Step 2 Illustrates the Synthesis of $CF_3(CF_2)_3(CH_2)_{11}I$

The pure fluorinated alcohol (57 mmol) from step 1 was dissolved in mixture of hexane (100 niL) and $Et_3N$ (171 mmol). To a stirred solution of alcohol methanesulfonyl chloride was added (114 mmol). After stirring for 2h, 100 mL water was added. The phases were separated, the organic part was washed with water (1×100 mL) and brine (1×100 mL), dried with $MgSO_4$ and evaporated to dryness. Crude mesylate was dissolved in 150 mL of acetone. Potassium iodide (171 mmol) was added and the mixture was refluxed for 12 h. After cooling, 100 mL of water was added, and the mixture was extracted with hexane (2×100 mL). The residue was purified by chromatography on silica gel using hexanes as the eluent. $^1$H—NMR (CDCl$_3$): 3.17 (t, 2H), 2.1–1.9 (m, 2H), 1.60 (m, 4H), 1.29(m, 14H).

Step 3 Illustrates the Synthesis of $CF_3(CF_2)_3(CH_2)_{11}N_3$

The pure fluorinated iodide (65 mmol) from step 2 was dissolved in DMF, and $NaN_3$ (130 mmol) was added as a solid. The suspension was stirred for 16 h at 80° C. After cooling, 100 mL of water was added, and the fluorinated azide was extracted with ether (2×150 mL). The organic phase was dried over $MgSO_4$. After evaporation of the solvent, the fluorinated azide was used for the next step without any additional purification. $^1$H—NMR (CDl$_3$): 3.26 (t 2H), 2.1–1.9 (m, 4H), 1.60 (m, 4H), 1.90 (m, 14H).

Step 4 Illustrates the Synthesis of $CF_3(CF_2)_3(CH_2)_{11}NH_2$

The azide (75 mmol) from step 3 was dissolved in 100 mL of THF and added to a suspension of $LiAlH_4$ (225 mmol) in THF(20 mL) at room temperature. The mixture was stirred for 3h, and after that, 150 mL of ice water was added. The reaction mixture was filtered, and the residue was washed with warm $CH_2Cl_2$. The layers were separated, and the aqueous layer was extracted twice with warm $CH_2Cl_2$. The combined organic layers were dried over $MgSO_4$. After evaporation of the solvents, the crude amine was purified by vacuum distillation. $^1$H—NMR (CDC13): 2.69 (t, 2H), 2.1–1.9 (m, 4H), 1.90 (m, 14H).

Example 2

This example illustrates the synthesis of $CF_3(CF_2)_3(CH_2)_{11}$NH—GLY—GLY—C(O)—$(CH_2)_2$SAc which incorporates a particular $R^{HB}$ group (NH—Gly—Gly—C(O)) as the hydrogen bonding moiety for a starting material of the present invention. This example involves a four step synthesis in which a GLY—GLY unit is prepared having a CO—$(CH_2)_2$—SAc tail and the fluorinated amine of Example 1 as the head.

Step 1 Illustrates the Synthesis of BnO—Gly—Gly—C(O)—$(CH_2)_2$—Br 4.79 g (31.3 mmol) 3-bromopropionic acid was dissolved in 30 mL of dry DMF. 3.23 g (15.7 mmol) N,N-dicyclohexylcarbodiimide (DCC) and 0.2 g DMAP were added to this solution at room temperature. After stirring for 1 h, the mixture was filtered and added to a solution of 6.18 g (15.7 mmol) GLY—GLY ester (as the toluenesulfonate salt) and 2.18 mL (15.7 mmol) triethylamine in 30 mL of dry DMF. The reaction mixture was stirred for 6 h at room temperature. After dilution in 200 mL ethylacetate, 200 mnL of water was added. The phases were separated, and the aqueous layer was extracted with ethyl acetate (3×50 mL). The combined organic phases were washed with a sat. aq. $NaHCO_3$ solution and brine, dried over $MgSO_4$ and evaporated. Recrystallization from ethanol gave 5.0 g (14.0 mmol, 89% yield) BnO—GLY—GLY—C(O)(CH$_2$)$_2$Br as a white powder. $^1$H—NMR (CD$_3$CN): 7.48–7.41 (m, 5H), 7.03 (br, 1H), 6.92 (br, 1H), 5.23 (s, 2H), 4.04 (d, J=6 Hz, 2H), 3.92 (d, J=6 Hz, 2H), 3.73 (t, J=6.6 Hz, 2H), 2.87 (t, J=6.6 Hz, 2H).

Step 2 Illustrates the Synthesis of GLY—GLY—C(O)(CH$_2$)$_2$Br 5.0 g (14.0 mmol) BnO—GLY—GLY—C(O)(CH2)2Br from step 1 wad dissolved in 250 mL ethanol. 500 mg palladium on carbon (10%) was added and the mixture was stirred under a hydrogen atmosphere for 3 h. After filtering through a small pad of Celite, the solvent was evaporated under vacuum. Recrystallization from acetonitrile yielded 2.63 g (9.85 mmol,70% yield) ofthe bromo acid as a white powder. $^1$H—NMR (CD$_3$CN*): 6.87 (br, 2H), 3.87 (d, J=6 Hz, 2H), 3.82 (d, J=6 Hz, 2H), 3.64 (t, J=6.6 Hz, 2H), 2.81 (t, J=6.6 Hz, 2H).

Step 3 Illustrates the Synthesis of GLY—GLY—C(O)(CH$_2$)$_2$SAc 2.63 g (9.85 mmol) bromo acid from step 2 was dissolved in 100 mL of dry ethanol. 1.24 g (10.83 mmol) potassium thioacetate was added and the mixture was stirred at 80° C. for 3 h. The solvent was evaporated under vacuum. The residue was re-dissolved in 1 00 mL of warm water and filtered. After evaporation to dryness, the residue was re-dissolved in 100 mL ethanol. Insoluble matter was removed by filtration and the product was crystallized by concentrating the ethanol solution. Yield: 1.71 g (6.52 mmol, 66%). $^1$H—NMR (D$_2$O): 3.84 (s, 2H), 3.80 (s, 2H), 2.97 (t, J=6.6 Hz, 2H), 2.49 (t, J=6.6 Hz, 2H), 2.20 (s, 3H).

Example 3

This example illustrates the synthesis of CF$_3$(CF$_2$)$_3$(CH$_2$)$_{11}$NH—GLY—GLY—C(O)—(CH$_2$)$_2$SH which is a particular surface modifying agents of the present invention where the R$^{HB}$ group begins with an amino functional group. This example involves a two step synthesis in which the amino starting material from Example 1 and the thioacetate starting material of Example 2 are reacted to form a thioacetate surface modifying agent intermediate which is converted to a thiol terminated surface modifying agent of the present invention by deprotection under basic conditions.

Step 1 Illustrates the Synthesis of CF$_3$(CF$_2$)$_3$(CH$_2$)$_{11}$NH—GLY—GLY—C(O)—(CH$_2$)$_2$—SAc The GLY—GLY-thioacetate (3.43 mmol) of Example 2 was dissolved in 10 mnL of DMF, and DCC (5.15 mmol) and DMAP (0.1 mol.%) were added. To stirred mixture was added a solution of the fluorinated amine of Example 1 in 10 mL of CH$_2$Cl$_2$. The mixture was stirred at room temperature for 40 h. After that, the mixture was diluted with 30 mL of hexane and filtered. The solid part was recrystallized from CHCl$_3$. Yield: 0.31 g of thioacetate, which was contaminated with urea. $^1$H—NMR(CDCl$_3$+CF$_3$COOH): 7.8 (b, 1H), 7.3 (b, 1H), 6.9 (b, lH), 4.08 (d, 2H), 4.04 (d, 2H), 3.27 (m, 2H), 3.16 (t, 2H), 2.67 (t, 2H1), 2.39 (s, 3H), 2.1–1.9 (m, 2H), 1.9 (m,18H).

Step 2 Illustrates the Synthesis of CF$_3$(CF$_2$)$_3$(CH$_2$)$_{11}$NH—GLY—GLY—C(O)—(CH$_2$)$_2$SH The fluorinated thioacetate of step 1 was dissolved in EtOH, and NaOH was added (1 equiv.). The mixture was mixed 15–20 min, and then acidified with conc. HCl. After dilution with water, the precipitate was filtered. The crude product was dissolved in a mixture of hot ethyl acetate and water. After filtration, the organic phase was collected and evaporated to dryness. The residue was recrystallized from ethanol. $^1$H—NMR (CDCl$_3$+CF$_3$COOH): 7.70 (b, 1lH), 7.10 (b, I1H), 6.79 (b,1H), 4.08 (d, 2H), 4.04 (d, 2H), 3.27(m, 2H), 2.93 (m, 2H), 2.77 (m, 2H), 2.1–1.9 (m, 2H), 1.8–1.4 (m, 3H), 1.25 (m, 16 H).

Example 4

This example illustrates the test results using CF$_3$(CF$_2$)$_3$(CH$_2$)$_{11}$NH—Gly—Gly—C(O)—(CH$_2$)$_2$SH deposited on a gold surface of a substrate.

CF$_3$(CF$_2$)$_3$(CH$_2$)$_{11}$NH—Gly—Gly—C(O)—(CH$_2$)$_2$SH was dissolved in ethanol and a monolayer on a gold surface was formed by adsorption at 60° C. for about 20 h. The ethanol was evaporated. The monolayer thickness was measured at between about 25.6Å and about 26.6Å.

TABLE I

Contact Angle Measurements

| Contact Angle for Water ($\Theta_a/\Theta_r$) | Conditions |
|---|---|
| 81/70 | after standard conditions |
| 78/66 | after treatment in Decalin at 90° C. for 30 minutes. |
| 15/0 | after treatment in Decalin at 120° C. for 30 minutes. |
| 78/68 | after treatment in air at 160° C. for 30 minutes. |
| 71/60 | after treatment in air at 200° C. for 10 minutes. |

Thus, the surface modified with the GLY—GLY surface modifying agent of Example 3 showed good retention of properties after high temperature air and solvent treatment.

REFERENCES

1. Brace, N. O. *J. Org. Chem.*, 1962, 27, 3027.
2. Brace, N. O. *J. Org. Chem.*, 1962, 27, 3033.
3. Brace, N. O.; vanElswyck, J. E. *J. Org. Chem.*, 1976, 41, 766.
4. Brace, N. O. *J. Fluorine Chem.*, 1982, 20, 3027.
5. Baum, K.; Bedford, C. D.; Hunadi, R. J. *J. Org. Chem.*, 1982, 47, 2251.
6. Fuchikami, T.; Ojima, I. *Tetrahedron Lett.* 1984, 25, 303.
7. Creary, X. *J. Org. Chem.*, 1987, 52, 5026.
8. Salvador, R. L.; Saucier, M. *Tetrahedron* 1971, 27, 1221.
9. Wagner, P. J.; Truman, R. J.; Puchalski, A. E.; Wake, R. J. *Am. Chem. Soc.* 1986, 108, 7727.
10. Ishikawa, N.; Koh, M. G.; Kitazume, T.; Choi, S. K. *J. Fluorine Chem.* 1984, 24, 419.
11. Uneyama, K.; Morimoto, O.; Yamshita, F. *Tetrahedron Lett.* 1989, 30, 4821.
12. Uneyama, K.; Momota, M. *Tetrahedron Lett.* 1989, 30, 265.
13. Takeyama, Y.; Ichinose; Y.; Oshima, K.; Utimoto, K. *Tetrahedron Lett.* 1989, 30 3139.
14. Meazza G.; Gapuzzi, L.; Picardi, P. *Synthesis* 1989, 331.
15. Burger, K.; Gaa, K.; Geith, K.; Schierlinger, C. *Synthesis* 1989, 850.
16. Kobayashi, Y.; Yamamoto, K.; Kumadaki, I. *Tetrahedron Lett.* 1979, 20 4071.
17. Park, J. D.; Lacher, J. R. *Photochemical Synthesis of Organic Fluorine Compounds*; Institution: W.A.D.C.T.R. 56–590, Pt.II; Report No. ASTIA No. 151014.
18. Moore, L.D. Dissertation Abstr. 1959, 20, 96.
19. Walling, C. *Free Radicals in Solution*; J. Wiley and Sons, Inc.: New York, 1957; pp 247.
20. Roedig, A in *Houben-Weyl, Methoden der organischen Chemie*; Georg Thieme Verlag, Stuttgart, 1060; pp 653.
21. Cloux, R.; Kovats, E.S. *Synthesis* 1992, 409.
22. Vol'pin, M.;Dvolaitzky, M.; Levitin, I. *Bull. Soc. Chim. Fr.* 1970, 1526.
23. Giese, B.; Jianing, H.; Mehl, W. *Chem. Ber.* 1988, 121, 2064.
24. Ulman, A. *An Introduction to Ultrathin Organic Films*; Academic: San Diego, 1991.
25. Whitesides, G.M.; Laibinis, P.E. *Langmuir* 1990, 6, 87.

All references and patents cited herein are incorporated herein by reference.

While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition comprising a surface modifying agent of Formula (III):

$$R_f\text{-}\omega Q \qquad (III)$$

where:
- Rf comprises a carbon-containing group including at least one fluorine atom;
- $\omega$ is selected from the group consisting of $R^1\text{-}R^{HB}\text{-}R^{XL}$, $R^{HB}\text{-}R^1\text{-}R^{XL}$, $R^{HB}\text{-}R^{XL}\text{-}R^1$, $R^1\text{-}R^{XL}\text{-}R^{HB}$, $R^{XL}\text{-}R^1\text{-}R^{HB}$, $R^{XL}\text{-}R^{HB}\text{-}R^1$, $R^1\text{-}R^{HB}\text{-}R^2\text{-}R^{XL}$, $R^{HB}\text{-}R^1\text{-}R^{XL}\text{-}R^2$, $R^1\text{-}R^{XL}\text{-}R^2\text{-}R^{HB}$, $R^{XL}\text{-}R^1\text{-}R^{HB}\text{-}R^2$, and combinations and mixtures thereof, where:
  - $R^1$ and $R^2$ are the same or different and are carbon-containing groups;
  - $R^{HB}$ is a group capable of intermolecular hydrogen bonding comprising a peptide linkage (—C(O)N(H)—), urethane linkage (—O—C(O)—N(H)—), urea linkage (—N(H)—C(O)—N(H)—) or mixtures or combinations thereof; and
  - $R^{XL}$ is a crosslinkable group selected from the groups consisting of an acetylenic group, a diacetylenic group, polyacetylenic group, an alpha amino acid group, an alpha hydroxy acid group or a dialkoxysilenyl group;
- Q comprises a group including at least one moiety capable of interacting with or bonding to a surface selected from the group consisting of $NR^3_2$, $OR^3$, $SiR^3_3$, $Si(OR^3)_3$, $PR^3_2$, $SR^3$ or $C(E^1)E^2$, where:
  - $R^3$ is a hydrogen atom or a carbon containing group, and
  - $C(E^1)E^2$ is selected from the group consisting of:
    - $C(NR^4)R^4$, $C(NR^4)NR^4_2$, $C(NR^4)OR^4$, $C(NR^4)PR^4_2$, $C(NR^4)SR^4$;
    - $C(O)R^4$, $C(O)NR^4_2$, $C(O)OR^4$, $C(O)PR^4_2$, $C(O)SR^4$;
    - $C(PR^4)R^4$, $C(PR^4)NR^4_2$, $C(PR^4)OR^4$, $C(PR^4)PR^4_2$, $C(PR^4)SR^4$;
    - $C(S)R^4$, $C(S)NR^4_2$, $C(S)OR^4$, $C(S)PR^4_2$, and $C(S)SR^4$;
    - and where each $R^4$ is the same or different and is a hydrogen atom or a carbon-containing group.

2. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is selected from the group consisting of $HN_2$, OH, $Si(OR^3)_3$, $PH_2$, SH and C(S)SH.

3. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is HN2.

4. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is OH.

5. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $Si(OR^3)_3$.

6. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $PH_2$.

7. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is SH.

8. The composition of claim 1, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between I and 20 carbon atoms and Q is C(S)SH.

9. The composition of claim 1, wherein $R^{XL}$ comprises a diacetylenic, $R^{HB}$ comprises a GLY—GLY group, $R^1$ and $R^2$ are linear carbon-containing groups having between 1 and 20 carbon atoms and Q is SH.

10. A substrate comprising a surface including a partial or complete monolayer comprising at least one surface modifying agent of Formula (III):

$$R_f\text{-}\omega Q \qquad (III)$$

where:
- $R_f$ comprises a carbon-containing group including at least one fluorine atom;
- $\omega$ is selected from the group consisting of $R^1\text{-}R^{HB}\text{-}R^{XL}$, $R^{HB}\text{-}R^1\text{-}R^{XL}$, $R^{HB}\text{-}R^{XL}\text{-}R^1$, $R^1\text{-}R^{XL}\text{-}R^{HB}$, $R^{XL}\text{-}R^1\text{-}$ $R^{HB}$, $R^{XL}-R^{HB}-R^1$, $R^1-R^{HB}-R^2-R^{XL}$, $R^{HB}-R^1-R^{XL}-R^2$, $R^1-R^{XL}-R^2-R^{HB}$, $R^{XL}-R^1-R^{HB}-R^2$, and combinations and mixtures thereof, where:

$R^1$ and $R^2$ are the same or different and are carbon-containing groups;

$R^{HB}$ is a group capable of intermolecular hydrogen bonding comprising a peptide linkage (—C(O)N(H)—), urethane linkage (—O—C(O)—N(H)—), urea linkage (—N(H)—C(O)—N(H)—) or mixtures or combinations thereof; and $R^{XL}$ is a crosslinkable group selected from the groups consisting of an acetylenic group, a diacetylenic group, polyacetylenic group, an alpha amino acid group, an alpha hydroxy acid group or a dialkoxysilenyl group;

Q comprises a group including at least one moiety capable of interacting with or bonding to a surface selected from the group consisting of $NR^3{}_2$, $OR^3$, $SiR^3{}_3$, $Si(OR^3)_3$, $PR^3{}_2$, $SR^3$ or $C(E^1)E^2$, where:

$R^3$ is a hydrogen atom or a carbon containing group, and $C(E^1)E^2$ is selected from the group consisting of:
$C(NR^4)R^4$, $C(NR^4)NR^4{}_2$, $C(NR^4)OR^4$, $C(NR^4)PR^4{}_2$, $C(NR^4)SR^4$;
$C(O)R^4$, $C(O)NR^4{}_2$, $C(O)OR^4$, $C(O)PR^4{}_2$, $C(O)SR^4$;
$C(PR^4)R^4$, $C(PR^4)NR^4{}_2$, $C(PR^4)OR^4$, $C(PR^4)PR^4{}_2$, $C(PR^4)SR^4$;
$C(S)R^4$, $C(S)NR^4{}_2$, $C(S)OR^4$, $C(S)PR^4{}_2$, and $C(S)SR^4$;

and where each $R^4$ is the same or different and is a hydrogen atom or a carbon-containing group.

11. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is selected from the group consisting of HN2, OH, $Si(OR^3)_3$, $PH_2$, SH and C(S)SH.

12. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is HN2.

13. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is OH.

14. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $Si(OR^3)_3$.

15. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $PH_2$.

16. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is SH.

17. The substrate of claim 10, wherein $R^{XL}$ comprises an acetylenic group, a diacetylenic group, polyacetylenic group, an alpha amino acid group, an alpha hydroxy acid, a dialkoxysilenyl group or mixtures or combinations thereof and R comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is C(S)SH.

18. The substrate of claim 10, wherein $R^{XL}$ comprises a diacetylenic, $R^{HB}$ comprises a GLY—GLY group, $R^1$ and $R^2$ are linear carbon-containing groups having between 1 and 20 carbon atoms and Q is SH.

19. A method comprising the step of contacting a substrate with at least one agent of Formula (III):

$$R_f\omega-Q \qquad (III)$$

where:

$R_f$ comprises a carbon-containing group including at least one fluorine atom;

ω is selected from the group consisting of $R^1-R^{HB}-R^{XL}$, $R^{HB}-R^1-R^{XL}$,
$R^{HB}-R^{XL}-R^1$, $R^1-R^{XL}-R^{HB}$, $R^{XL}-R^{HB}-R^1$, $R^1-R^{HB}-R^2-R^{XL}$, $R^{HB}-R^1-R^{XL}-R^2$, $R^1-R^{XL}-R^2-R^{HB}$, $R^{XL}-R^1-R^{HB}-R^2$, and combinations and mixtures thereof, where:

$R^1$ and $R^2$ are the same or different and are carbon-containing groups;

$R^{HB}$ is a group capable of intermolecular hydrogen bonding comprising a peptide linkage (—C(O)N(H)—), urethane linkage (—O—C(O)—N(H)—), urea linkage (—N(H)—C(O)—N(H)—) or mixtures or combinations thereof; and $R^{XL}$ is a crosslinkable group selected from the groups consisting of an acetylenic group, a diacetylenic group, polyacetylenic group, an alpha amino acid group, an alpha hydroxy acid group or a dialkoxysilenyl group;

Q comprises a group including at least one moiety capable of interacting with or bonding to a surface selected from the group consisting of $NR^3{}_2$, $OR^3$, $SiR^3{}_3$, $Si(OR^3)_3$,
$PR^3{}_2$, $SR^3$ or $C(E^1)E^2$, where:

$R^3$ is a hydrogen atom or a carbon containing group, and $C(E^1)E^2$ is selected from the group consisting of:

$C(NR^4)R^4$, $C(NR^4)NR^4_2$, $C(NR^4)OR^4$, $C(NR^4)PR^4_2$, $C(NR^4)SR^4$;

$C(O)R^4$, $C(O)NR^4_2$, $C(O)OR^4$, $C(O)PR^4_2$, $C(O)SR^4$;

$C(PR^4)R^4$, $C(PR^4)NR^4_2$, $C(PR^4)OR^4$, $C(PR^4)PR^4_2$, $C(PR^4)SR^4$;

$C(S)R^4$, $C(S)NR^4_2$, $C(S)OR^4$, $C(S)PR^4_2$, and $C(S)SR^4$;

and where each $R^4$ is the same or different and is a hydrogen atom or a carbon-containing group, where the contacting forms a partial or complete monolayer of the at least one compound on a surface of the substrate.

20. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is selected from the group consisting of $HN_2$, OH, $Si(OR^3)_3$, $PH_2$, SH and C(S)SH.

21. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $HN_2$.

22. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is OH.

23. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $Si(OR^3)_3$.

24. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is $PH_2$.

25. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is SH.

26. The method of claim 19, wherein $R^{XL}$ comprises an acetylenic group, a diacetylenic group, polyacetylenic group, an alpha amino acid group, an alpha hydroxy acid, a dialkoxysilenyl group or mixtures or combinations thereof and $R^{HB}$ comprises a peptide linkage (—C(O)N(H)—), urethane linkage (—O—C(O)—N(H)—), urea linkage (—N(H)—C(O)—N(H)—) or mixtures or combinations thereof and $R^1$ and $R^2$ are linear carbon-containing groups having between 1 and 20 carbon atoms and Q is C(S)SH.

27. The method of claim 19, wherein $R^{XL}$ comprises a diacetylenic, $R^{HB}$ comprises a GLY—GLY group, $R^1$ and $R^2$ are linear carbon-containing groups having between 1 and 20 carbon atoms and Q is SH.

* * * * *